(12) United States Patent
Bassi et al.

(10) Patent No.: US 8,083,350 B2
(45) Date of Patent: Dec. 27, 2011

(54) LIGHT SENSITIVITY METER AND USES THEREOF

(75) Inventors: Carl J. Bassi, St. Louis, MO (US);
Michael Howe, St. Charles, MO (US);
Wayne P. Garver, St. Louis, MO (US)

(73) Assignee: The Curators of the University of Missouri, St. Louis, MO (US)

( * ) Notice: Subject to any disclaimer, the term of this patent is extended or adjusted under 35 U.S.C. 154(b) by 609 days.

(21) Appl. No.: 12/094,566

(22) PCT Filed: Nov. 21, 2006

(86) PCT No.: PCT/US2006/061138
§ 371 (c)(1),
(2), (4) Date: Oct. 28, 2008

(87) PCT Pub. No.: WO2007/062367
PCT Pub. Date: May 31, 2007

(65) Prior Publication Data
US 2009/0153800 A1    Jun. 18, 2009

Related U.S. Application Data

(60) Provisional application No. 60/738,501, filed on Nov. 21, 2005.

(51) Int. Cl.
*A61B 3/14* (2006.01)
(52) U.S. Cl. ........................ 351/210; 351/246
(58) Field of Classification Search .......... 351/210–211, 351/246
See application file for complete search history.

(56) References Cited

U.S. PATENT DOCUMENTS

| 2,482,669 A | 9/1949 | Harding |
| 4,511,228 A | 4/1985 | von Gierke et al. |

(Continued)

FOREIGN PATENT DOCUMENTS

WO    2005094667 A2    10/2005

OTHER PUBLICATIONS

Main et al., "The Wavelength of Light Causing Photophobia in Migraine and Tension-type Headache Between Attacks," European Institute of Health and Medical Sciences, Mar. 2000, pp. 194-199.

(Continued)

*Primary Examiner* — James Greece
(74) *Attorney, Agent, or Firm* — Senniger Powers LLP

(57) ABSTRACT

A text apparatus for measuring the degree of light-sensitivity of a subject, such as a subject with cataracts or migraines. The apparatus comprises a viewing shroud for positioning at least one eye of the subject in a testing position and an illumination source adapted for emitting visible light toward the at least one eye of the subject. The apparatus includes a visual monitor adapted for monitoring the fixation of the at least one eye during testing. A method of the invention exposes at least one eye of a subject to light and either subjects the eye to a continuous, level light intensity or increases the intensity of the light continuously over time. The intensity of the light when the subject experiences discomfort can be recorded. Pulse width modulation can modulate the intensity of the illumination source (e.g., an LED) over time.

16 Claims, 3 Drawing Sheets

U.S. PATENT DOCUMENTS

| | | | |
|---|---|---|---|
| 5,108,170 A * | 4/1992 | Sugiyama | 351/226 |
| 5,506,633 A | 4/1996 | Sperling | |
| 5,750,983 A | 5/1998 | Swanson | |
| 5,910,834 A | 6/1999 | McClure et al. | |
| 6,099,126 A * | 8/2000 | Teskey | 351/213 |
| 6,315,412 B1 * | 11/2001 | Snodderly et al. | 351/200 |
| 6,592,222 B2 | 7/2003 | Massengill et al. | |
| 6,606,577 B1 | 8/2003 | Fukuhara | |
| 6,834,958 B2 | 12/2004 | Cornsweet et al. | |
| 6,916,096 B2 | 7/2005 | Eberl et al. | |
| 7,156,518 B2 | 1/2007 | Cornsweet et al. | |
| 2004/0263780 A1 * | 12/2004 | Hu et al. | 351/205 |
| 2005/0094099 A1 | 5/2005 | Newman et al. | |
| 2006/0077348 A1 | 4/2006 | Gorin | |
| 2006/0238704 A1 | 10/2006 | Donnerhacke et al. | |
| 2007/0121071 A1 * | 5/2007 | Jackson et al. | 351/246 |

OTHER PUBLICATIONS

Vanagaite et al., "Light-induced Discomfort and Pain in Migraine," Department of Neurology, University Hospital of Trondheim, printed on Aug. 21, 2006, 14 pages.

Drummond, "A Quantitative Assessment of Photophobia in Migraine and Tension Headache," Department of Neurology, Prince Henry Hospital, May 1, 1986, 5 pages.

Adams et al., "The Evaluation of Light Sensitivity in Benign Essential Blepharospasm," American Journal of Ophthalmology, Jul. 2006, 1 page.

Lutzi et al., "Tinted Hydrogel Lenses: An Assessment of Glare Sensitivity Reduction," School of Optometry, University of Waterloo, Jul. 1985, pp. 478-481.

* cited by examiner

LIGHT SENSITIVITY METER AND USES THEREOF

FIELD OF THE INVENTION

The present invention relates to an instrument and method for measurement of light sensitivity in subjects. More particularly, the present invention directs to a device for quantified measurement of light hypersensitivity/photophobia of a person.

BACKGROUND OF THE INVENTION

Light hypersensitivity is characterized by pain, tearing, reflexive squinting, and/or photophobia in response to changes (typically increases) in illumination. Often a person experiences light hypersensitivity when exposed to sunlight, but sometimes, a patient may experience similar symptoms in response to small changes in illumination such as turning on room lights or even turning on computer monitors. In serious cases, some people suffering light hypersensitivity find it necessary to wear sunglasses or other filters (such as blue-blocker filters) at all times. In the most serious cases, a patient may have to avoid lighted spaces altogether.

Light hypersensitivity has been found in many patient populations including, but not limited to, cataracts or migraines. Light hypersensitivity can also be found in people taking photosensitizing drugs, such as phenothiazines, chloroquine or vidarabine, or medications that affect pupil size, such as amphetamines, atropine, cyclopentolate, phenylepherine, scopolamine, and tropicamide, to name a few. Other patient populations with light hypersensitivity include, but are not limited to a variety of clinical conditions such as refractive surgery, chalazion, glaucoma, iritis, corneal abrasion, corneal ulcer, and uveitis.

A patient with light hypersensitivity is currently classified as "light sensitive" or "photophobic" by clinicians. However, no reliable instrument or method is currently available to measure the degree of light hypersensitivity in a patient. Therefore, it is desirable to have a new device and innovative methods of using such a device, to provide quantitative measurements.

SUMMARY OF THE INVENTION

Aspects of the present invention permit quantitative measurements of a patient's light hypersensitivity. In particular, one or both eyes of a patient are exposed to a series of lights of various intensities (i.e., brightness). When one or both eyes of the patient experience discomfort during the exposures, the light intensity is recorded and later evaluated by a clinician.

A method embodying aspects of the invention provides a quantitative measurement of light hypersensitivity in a patient. The inventive method comprises the steps of: (1) exposing one or both eyes of a subject to a series of light, (2) adjusting the intensities of the light, and (3) recording the intensity when the subject experiences discomfort.

An aspect of the aforesaid adjusting step further comprises the step of increasing the light intensities manually. Another aspect of the aforesaid adjusting step further comprises increasing the light intensities by a series of pre-determined intensity increments over a pre-determined time period. Yet another aspect of the aforesaid adjusting step further comprises the steps of (a) setting the light intensity at a pre-determined level, and (b) emitting a series of light pulses at the pre-determined intensity.

Further aspects of the invention provide a device or instrument for quantitatively measuring light hypersensitivity in a patient. The inventive device, the "light sensitivity meter" (LSM), comprises an illumination source capable of emitting light with fixed or variable intensity of visible wavelengths and a viewing shroud for containing the emitted light and exposing one or both eyes of a subject to the light. The viewing shroud provides a means to control stimulus conditions including ambient light levels and proper viewing distance.

In one exemplary aspect, the inventive instrument further comprises a light emitting diode (LED) matrix display as the illumination source, an intensity adjustment means to adjust the intensity of the emitted light, a photosensor to measure the intensity of the light at the position of the subject's eyes, and a means to allow a user (such as a clinician administering the measurements) to monitor the subject's fixation during measurements.

In another exemplary aspect, a method for measuring the degree of light sensitivity of a subject comprises receiving a selection for a predetermined light intensity. The method positions at least one eye of a subject to receive light at the selected pre-determined light intensity and emits a series of light pulses at a frequency approximating continuous light when viewed by the subject. The light pulses, individually, have at a higher light intensity than the pre-determined light intensity, whereby the subject perceives the intensity of the higher intensity light pulses as continuous light at the pre-determined light intensity. In still another aspect, the subject perceives the intensity of the higher intensity light pulses as continuous light at an average light intensity.

DETAILED DESCRIPTION OF THE INVENTION

Figure 1:
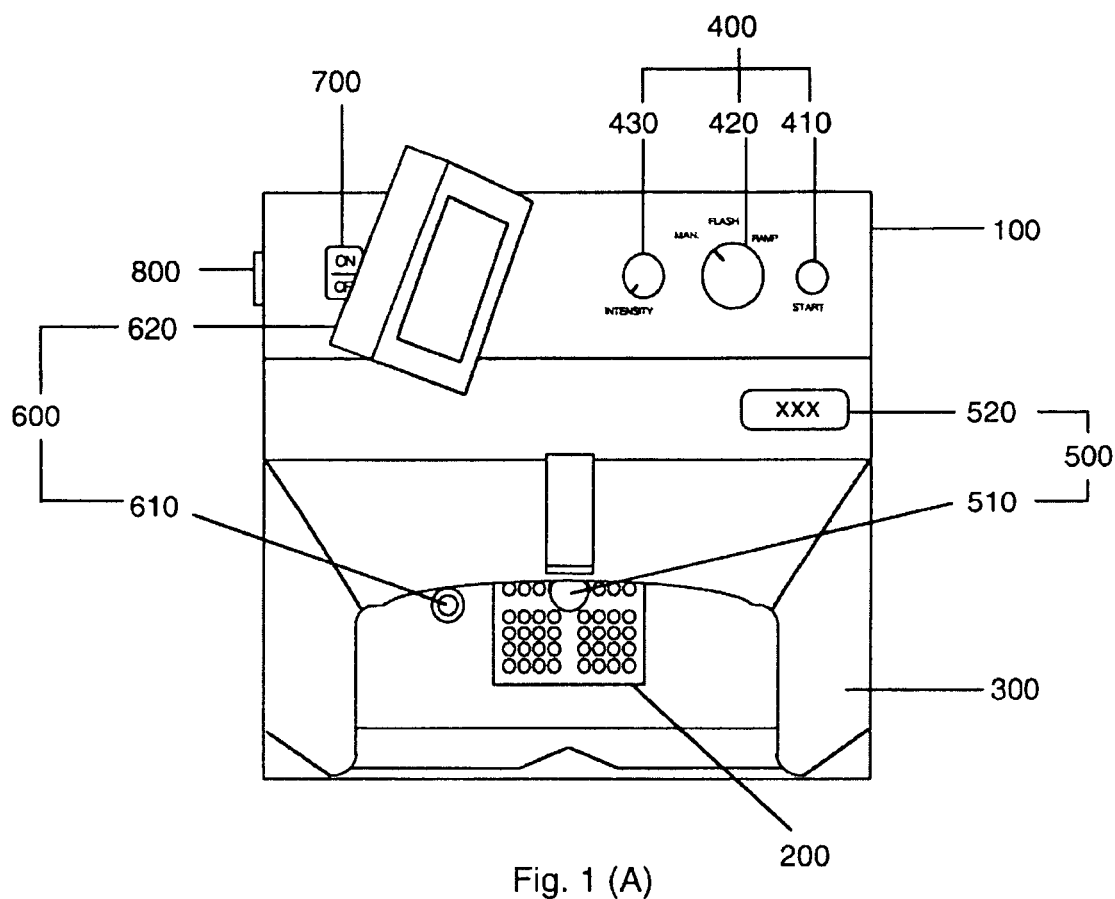
FIG. 1(A) is a top view of one exemplary embodiment of the inventive light sensitivity meter.
FIG. 1(B) is a side view of the exemplary embodiment of the inventive light sensitivity meter of FIG. 1(A).
FIG. 1(C) is a front view of the exemplary embodiment of the inventive light sensitivity meter of FIG. 1(A).
FIG. 1(D) is a back view of the exemplary embodiment of the inventive light sensitivity meter of FIG. 1(A).
Figure 1:
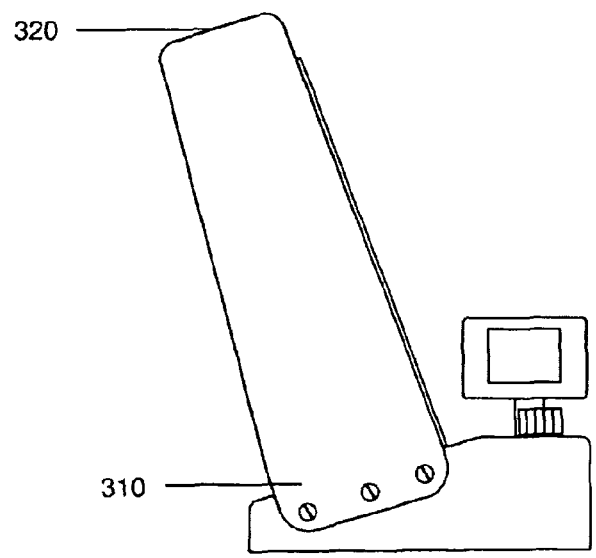
Figure 1:
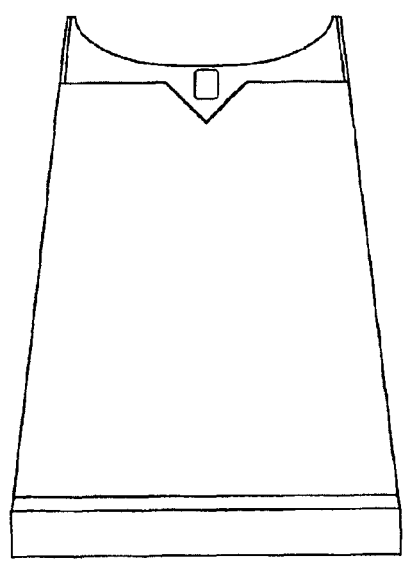
Figure 1:
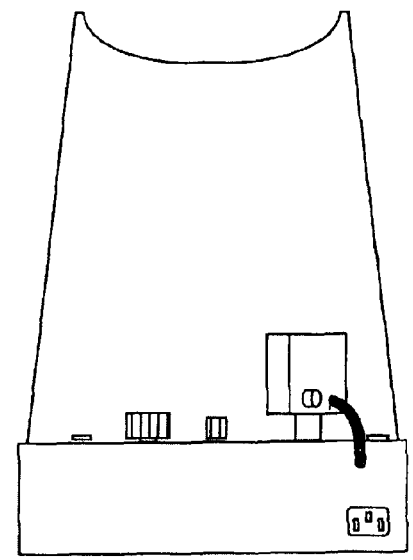

As stated above, the aspects of the present invention provide a novel device, the "Light Sensitivity Meter" (LSM), for quantitative measurement of a subject's light hypersensitivity. The inventive LSM comprises an illumination source capable of emitting light with fixed or variable intensity at visible wavelengths and a viewing shroud with a light opening and an ocular opening, where the light opening allows the emitted light to travel though and reach the ocular opening for viewing by the subject.

The illumination source can be any light source capable of emitting light at visible wavelengths (between approximately 400 nm to about 700 nm). For example, the light source can be an incandescent or xenon light. However, ideally the light stimulus should be at least in part comprised of short wavelengths (about 400 nm to 500 nm).

In one embodiment, the illumination source comprises one or more light emitting diodes (LEDs) arranged in, for example, an LED matrix display, i.e., a certain combination of multiple LEDs. Such an LED matrix display with LEDs that have a relatively high short wavelength spectral content provides advantages over other light sources. For example, the LED matrix offers desirable spectral content and flexible matrix combinations of wavelengths and intensities. Specifically, the LED matrix provides stable and consistent intensity, and the intensities can be easily modulated. The LED matrix also requires relatively low power and generates very low heat during the testing. The suitable LEDs include white LEDs with a high intensity, short wavelength (approximately 460 nm) component.

The inventive LSM can further include a means to adjust intensities of the emitted light, "intensity adjustment means." Intensity adjustment is by means of pulse width modulation where the LEDs are turned on periodically to maximum intensity for a certain fraction of the period and turned off periodically for the remaining fraction of the period. The subject perceives the average intensity of the light source if the period is less than 20 milliseconds. Moreover, the frequency of pulse width modulation may be selected such that the subject perceives the pulsed light as continuous (e.g., faster than about 50 Hz).

The viewing shroud is employed to contain and reflect the emitted light, prevent exposing subject's eye(s) to other sources of light (such as ambient light in the surrounding environment), and set the desired viewing angle. The viewing shroud includes at least two openings: a light opening and an ocular opening. The light opening allows the emitted light to pass though and reach the ocular opening. The ocular opening serves as a headrest for the subject being examined. The size and shape of the ocular opening will allow the subject's eyes to be exposed to the emitted light. The viewing distance, i.e. the distance between the subject's eye and the illumination source, and the size of the tight source determine the viewing angle. In one exemplary embodiment, the viewing angle is about 10.5 degrees.

The inventive LSM can further comprise a photosensor to measure intensities of the emitted light as viewed by the subject during testing. The photosensor can be located at or near the second opening of the viewing means. The photosensor should be sensitive to visible light intensities from the source and provide absolute calibration of intensity levels. The inventive LSM can further provide a means to monitor the subject's fixation and to monitor the patient's response.

The present invention further discloses an exemplary embodiment of the LSM, as shown in FIGS. 1(A) to 1(D). FIG. 1(A) is a top view of the exemplary embodiment. The exemplary embodiment comprises:

(1) a base body (100);
(2) an illumination source (200) mounted on the base body (100);
(3) a viewing shroud (300) with at least two openings, where a first opening, a light opening (310), opens to the illumination source (200) so that the emitted light passes into the viewing shroud (300), and a second opening, an ocular opening (320), exposes one or both eyes of a testing subject to the emitted light and serves as a headrest for the testing subject;
(4) intensity adjustment means (400) mounted on the base body (100) and electronically connected with the illumination source (200) so that the intensity adjustment means can adjust the intensity of the emitted light;
(5) photo-sensing means (500) with a photosensor (510) positioned at or near the ocular opening (330) to detect intensities of the emitted light viewed by the subject and a sensor readout (520) located on the base body (100) and in electronic connection with the photosensor (510); and (6) monitor means (600), or visual monitor, with a video camera (610) located inside of the viewing shroud (300) for imaging one or both eyes of a testing subject, and a video monitor (620) mounted on the base body (100) that enables a user administering the testing to monitor the subject's fixation during testing.

FIG. 1(B), FIG. 1(C), and FIG. 1(D) are the side, front, and back views of the exemplary embodiment, respectively, which provide further illustration of the setup of the embodiment and the locations and associations of different components of the embodiment.

In the foresaid exemplary embodiment, the base body (100) can be made of any material that provides adequate support for the components attached to it. Optionally, the base body can also serve as a housing means to contain all or some of the hardware needed for other components. Advantageously, base body (100) provides a compact, portable housing.

Figure 2:
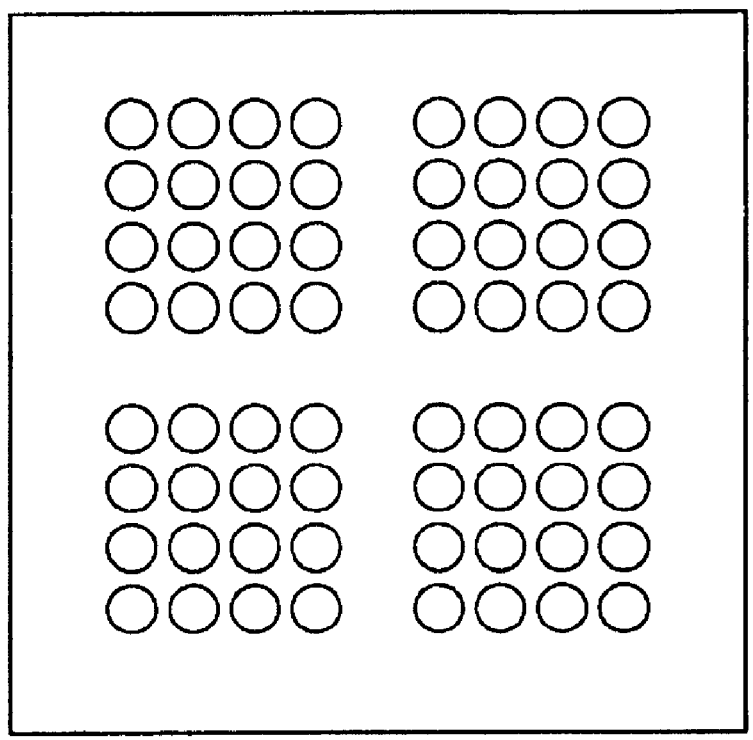
FIG. 2 is a diagram illustrating an LED matrix display employed in another exemplary embodiment of the inventive light sensitivity meter.

The illumination source (200) of the exemplary embodiment employs the LED matrix display. In the exemplary embodiment, the individual LEDs employed are about 5 millimeters in diameter, and the total number of LEDs is 64. The LEDs are arranged in four 4×4 arrays, as shown in FIG. 2. This array provides enough intensity for inducing the light sensitivity response of subject's eyes, and the cross-shaped results in a fixation point for the subject to observe.

Moreover, the exemplary embodiment uses a white opaque polycarbonate to reflect the internal light for the viewing shroud (300). The viewing shroud (300) is shaped to shield the subject from ambient light and to provide a headrest for a fixed viewing distance of the stimulus. The viewing shroud can be mounted at the light opening (310) on the base body (100).

The intensity adjustment means (400) includes a mode switch (420), an intensity control (430), and a start switch (410). The intensity control (430) uses pulse width modulation to modulate the intensity so that the LEDs' spectral contents are constant at all intensities. The mode switch (420) provides three modes of operation: MAN (manual), FLASH, and RAMP. During manual mode operation, the mode switch (420) is set to MAN, and a user can adjust the light intensities by manually turning the intensity control. During flash mode operation, the desired flash intensity is first set when the mode switch (420) is first set at MAN. The mode switch (420) is then set to FLASH. When the start switch (410) is activated, the LED light source (200) will pulse once for a pre-set duration, such as about 500 milliseconds, at an intensity previously set. During ramp mode operation, the mode switch (420) is set to RAMP. When the start switch (410) is activated, the LED light source (200) increases in intensity from "0," i.e. no light emitted, to its maximum over a pre-set time period, such as about 22 seconds. If at any time during the testing the subject experiences discomfort, due to changes in illumination/intensity for example, the subject can simply notify the user or activate the optional stop selector, or switch, (800). After the activation of the stop switch, the LED light source (200) will halt its increase in intensity and remain at that particular intensity for several seconds, such as about 6 seconds (to allow the user to record the intensity). As would be readily understood by one skilled in the art, the LSM may automatically record the intensity when the user or the subject activates the stop switch.

The photosensor (510) is located on or near the ocular opening (330) of the viewing shroud (300), so that the photosensor can record accurate readings of intensities of the light viewed by the subject's eye(s). The sensor readout (520) can either display numeric readouts for a user to record, or be electronically connected with a data storage/analysis means for further analysis at a user's option.

The visual monitor (600) with the video camera (610) and video monitor (620) is located inside the viewing shroud (300) and on the base body (100), respectively, which makes the exemplary embodiment a relatively compact, portable unit for users' convenience. However, certain part(s) of the visual monitor, such as the video monitor (620), can be optionally located elsewhere other than the base body (100).

The exemplary embodiment also comprises additional features for users' convenience. For example, the exemplary embodiment employs a main power source with its on/off switch (700) located on the base body (100), as illustrated in FIG. 1(A). The centrally located power source provides power to all components and makes the exemplary embodiment a portable unit. The exemplary embodiment also comprises a stop switch, which users administering the testing or test subjects can activate when light intensities reach levels of discomfort. The light intensity remains constant following activation of the stop switch. An optional speaker sounds a tone whenever the stop switch is activated.

Embodiments of the present invention also provide an inventive method to use the inventive light sensitivity meter. The inventive method comprises the steps of:
(1) exposing one or both eyes of a subject to a series of light,
(2) adjusting the intensity of the light, and
(4) recording the intensity when the subject experiences discomfort.

An embodiment of the aforesaid adjusting step further comprises the step of changing the intensity of the emitted light continuously. In practice when using the aforesaid exemplary embodiment of the inventive light sensitivity meter, the mode switch (420) is sot at MAN (the manual mode), and the intensity switch (430) is operated by a user to adjust the light intensity.

Another embodiment of the aforesaid adjusting step further comprises increasing the intensity of the emitted light by a series of pre-determined intensity increments over a pre-determined time period. When using the exemplary embodiment, the mode switch (420) is set at the RAMP, the start switch (430) is activated, and the illumination source (200) automatically delivers the predetermined light increments from 0%-100% intensity over a time of about 22 seconds.

Yet another embodiment of the aforesaid adjusting step further comprises the steps of (a) setting the intensity of the emitted light at a pre-determined level, and (b) emitting an approximately 500 millisecond light pulse of the pre-determined intensity. When using the exemplary embodiment, the mode switch is first set to MAN, the light intensity level is set by adjusting the intensity switch (430), the mode switch (420) is then set to FLASH, and the start switch (410) is activated to instruct the illumination source (200) to emit a light pulse.

While the invention has been described in connection with specific embodiments thereof, it will be understood that the light sensitivity meter is capable of further modifications, and so does the method of using the sensitivity meter. This patent application is intended to cover any variations, uses, or adaptations of the invention following, in general, the principles of the invention and including such departures from the present disclosure as come within known or customary practice within the art to which the invention pertains and as may be applied to the essential features herein before set forth and as follows in scope of the appended claims.

What is claimed is:

1. A test apparatus for measuring the degree of light sensitivity of a subject comprising:

a viewing shroud adapted for positioning the subject in a testing position, said viewing shroud shaped to shield a at least one eye of the subject from ambient light in a surrounding environment when the subject is in the testing position;
an illumination source for emitting visible light into the viewing shroud during testing, said visible light being emitted toward the at least one eye of the subject when the subject is in the testing position, wherein an intensity of the emitted visible light of the illumination source is modulated so that the spectral content of the light remains substantially constant at all intensities; and
a visual monitor for monitoring the fixation of the at least one eye on the visible light during testing.

2. The apparatus as set forth in claim 1 wherein said visual monitor comprises a video camera for imaging said at least one eye.

3. The apparatus as set forth in claim 2 wherein said visual monitor comprises a video monitor for monitoring the fixation of the at least one eye during testing.

4. The apparatus as set forth in claim 1 further comprising a photosensor for sensing the intensity of the light emitted into the viewing shroud for viewing by the at least one eye of the subject during testing.

5. The apparatus as set forth in claim 1 wherein said illumination source comprises at least one LED.

6. The apparatus as set forth in claim 5 wherein said illumination source comprises an LED matrix display.

7. The apparatus as set forth in claim 1 wherein the intensity of the emitted visible light of the illumination source is modulated with pulse width modulation.

8. The apparatus as set forth in claim 1 further comprising a compact, portable housing for maintaining the viewing shroud, the illumination source, and the visual monitor in a compact and portable space.

9. A method for measuring the degree of light sensitivity of a subject comprising:
exposing at least one eye of a subject to light;
increasing the intensity of the light continuously over time;
modulating the intensity of the light so that the spectral content of the light remains substantially constant at all intensities;
receiving a notification from the subject when the subject experiences discomfort due to the intensity of the light;
in response to receiving the notification from the subject, halting the increasing of the intensity of the light; and
recording the intensity of the light when the subject experiences discomfort due to the intensity of the light.

10. The method of claim 9 wherein said increasing the intensity of the light continuously over time comprises increasing the intensity of the light by a series of pre-determined intensity increments over a pre-determined period.

11. The method of claim 9 wherein said modulating the intensity of the light comprises modulating the intensity of the light with pulse width modulation.

12. The method of claim 9 wherein said modulating the intensity of the light comprises modulating the light emitted by at least one LED.

13. A method for measuring the degree of light sensitivity of a subject comprising:
during a manual mode, receiving a selection for a pre-determined light intensity;
during a flash mode, emitting a pulse of light at the pre-determined light intensity;
during a ramp mode, positioning at least one eye of a subject to receive light and emitting light having an intensity that increases from a minimal intensity to the pre-determined light intensity, wherein the light emitted which has the pre-determined light intensity comprises a series of light pulses at a frequency approximating continuous light when viewed by the subject, said light pulses individually having a higher light intensity than the pre-determined light intensity, whereby the subject perceives the intensity of the higher intensity light pulses as continuous light at the pre-determined light intensity; and determining whether the subject experiences discomfort during the ramp mode due to changes in the light intensity.

14. A method as set forth in claim 13 wherein the series of light pulses is emitted from an LED at the maximum intensity of the LED.

15. A method as set forth in claim 14 whereby the subject perceives the intensity of the higher intensity light pulses as continuous light at an average light intensity.

16. A method as set forth in claim 13 wherein the subject perceives the intensity of the light pulses as continuously increasing light intensity over time according to the pre-determined light intensity increase.

* * * * *